US009072816B2

(12) United States Patent
Matheny (10) Patent No.: US 9,072,816 B2
(45) Date of Patent: *Jul. 7, 2015

(54) COMPOSITION FOR MODULATING INFLAMMATION OF CARDIOVASCULAR TISSUE

(71) Applicant: CORMATRIX CARDIOVASCULAR, INC., Roswell, GA (US)

(72) Inventor: Robert Matheny, Norcross, GA (US)

(73) Assignee: CORMATRIX CARDIOVASCULAR, INC., Roswell, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/573,569

(22) Filed: Sep. 24, 2012

(65) Prior Publication Data

US 2013/0058904 A1 Mar. 7, 2013

Related U.S. Application Data

(63) Continuation-in-part of application No. 13/328,287, filed on Dec. 16, 2011.

(51) Int. Cl.

| | | |
|---|---|---|
| A61K 9/14 | (2006.01) |
| A61K 35/12 | (2015.01) |
| A61F 2/00 | (2006.01) |
| A61K 9/48 | (2006.01) |
| C12N 5/02 | (2006.01) |
| A61L 27/36 | (2006.01) |
| A61K 48/00 | (2006.01) |
| A61L 27/38 | (2006.01) |
| A61K 31/165 | (2006.01) |
| A61K 31/4174 | (2006.01) |
| A61K 31/43 | (2006.01) |
| A61K 31/505 | (2006.01) |
| A61K 31/65 | (2006.01) |
| A61K 31/7048 | (2006.01) |
| A61K 31/7056 | (2006.01) |
| A61K 35/34 | (2015.01) |
| A61K 38/14 | (2006.01) |
| A61K 45/06 | (2006.01) |
| A61K 31/22 | (2006.01) |
| A61K 31/366 | (2006.01) |
| A61K 31/40 | (2006.01) |
| A61K 31/404 | (2006.01) |
| A61K 31/4418 | (2006.01) |
| A61K 31/47 | (2006.01) |
| A61K 31/722 | (2006.01) |
| A61K 35/38 | (2015.01) |
| A61K 9/00 | (2006.01) |

(52) U.S. Cl.
CPC ........... *A61L 27/3633* (2013.01); *A61K 9/0019* (2013.01); *A61K 48/00* (2013.01); *A61L 27/367* (2013.01); *A61L 27/3683* (2013.01); *A61L 27/3873* (2013.01); *A61L 2400/06* (2013.01); *A61L 2430/20* (2013.01); *A61K 31/165* (2013.01); *A61K 31/4174* (2013.01); *A61K 31/43* (2013.01); *A61K 31/505* (2013.01); *A61K 31/65* (2013.01); *A61K 31/7048* (2013.01); *A61K 31/7056* (2013.01); *A61K 35/34* (2013.01); *A61K 38/14* (2013.01); *A61K 45/06* (2013.01); *A61K 31/22* (2013.01); *A61K 31/366* (2013.01); *A61K 31/40* (2013.01); *A61K 31/404* (2013.01); *A61K 31/4418* (2013.01); *A61K 31/47* (2013.01); *A61K 31/722* (2013.01); *A61K 35/38* (2013.01)

(58) Field of Classification Search
USPC .................. 424/484, 423, 551; 435/387, 395
See application file for complete search history.

(56) References Cited

U.S. PATENT DOCUMENTS

| | | | | |
|---|---|---|---|---|
| 5,275,826 A | * | 1/1994 | Badylak et al. ................ 424/551 |
| 6,096,347 A | * | 8/2000 | Geddes et al. ................ 424/551 |
| 6,375,989 B1 | * | 4/2002 | Badylak et al. ................ 424/551 |
| 7,914,808 B2 | * | 3/2011 | Malaviya et al. ............. 424/423 |
| 8,003,131 B2 | * | 8/2011 | Badylak ........................ 424/553 |
| 8,409,625 B2 | * | 4/2013 | Badylak ........................ 424/574 |
| 2006/0002979 A1 | * | 1/2006 | Ashammakhi et al. ........ 424/426 |
| 2006/0147433 A1 | * | 7/2006 | Hiles ............................. 424/93.7 |
| 2006/0293760 A1 | * | 12/2006 | DeDeyne ................... 623/23.76 |
| 2010/0233235 A1 | | 9/2010 | Matheny et al. |
| 2010/0266654 A1 | | 10/2010 | Hodde et al. |
| 2012/0156255 A1 | * | 6/2012 | Singh et al. ................... 424/400 |

OTHER PUBLICATIONS

Rosso et al., From Cell-ECM interaction to Tissue Engineering 2004; Journal of Cellular Physiology 174-180.*
Badylak et al., 2003, Extracellular Matrix for Myocaridal Repair The heart surgery forum pp. 20-26.*
Badylak et al 2009 Extracellular matrix as a biological scaffold material: Structure and function Acta Biomaterialia 5 (2009) 1-13.*
Zhao et al Improvement in Cardiac Function With Small Intestine Extracellular Matrix is Associated With Recruitment of C-Kit Cells, Myofibroblasts, and Macrophages After Myocardial Infarction Journal of the American College of Cardiology vol. 55, Issue 12, Mar. 23, 2010, pp. 1250-1261.*
Ji et al Effect of preoperative atorvastatin therapy on atrial fibrillation following off-pump coronary artery bypass grafting Circ J. Dec. 2009;73(12):2244-9. Epub Oct. 13, 2009.*
Collard, C.D., et al. Preoperative statin therapy is associated with reduced cardiac mortality after coronary artery bypass graft surgery, J Thorac Cardiovasc Surg 132, 392-400 (2006).*
Liakopoulos, O.J., et al. Impact of preoperative statin therapy on adverse postoperative outcomes in patients undergoing cardiac surgery: a meta-analysis of over 30,000 patients, Eur Heart J 29, 1548-1559 (2008).*
Thielmann, M., et al. Lipid-lowering effect of preoperative statin therapy on postoperative major adverse cardiac events after coronary artery bypass surgery, J Thorac Cardiovasc Surg 134, 1143-1149 (2007).*

* cited by examiner

*Primary Examiner* — Maria Leavitt
(74) *Attorney, Agent, or Firm* — Francis Law Group (57) ABSTRACT

A composition for reconstruction, replacement or repair of damaged or diseased biological tissue comprising an extracellular matrix (ECM) composition that includes an ECM scaffold component derived from a mammalian source and at least one additional bioactive component selected from the group consisting of a statin and a chitin derivative.

2 Claims, 2 Drawing Sheets

COMPOSITION FOR MODULATING INFLAMMATION OF CARDIOVASCULAR TISSUE

CROSS-REFERENCES TO RELATED APPLICATIONS

This application is a continuation-in-part of U.S. application Ser. No. 13/328,287, filed on Dec. 16, 2011, which claims the benefit of U.S. Provisional Application No. 61/425,287, filed on Dec. 20, 2010.

FIELD OF THE INVENTION

The present invention relates to methods for treating biological tissue. More particularly, the present invention relates to methods and systems for treating damaged and diseased biological tissue; particularly, cardiovascular tissue.

BACKGROUND OF THE INVENTION

Myocardial infarction is a common presentation of ischemic heart disease/coronary artery disease. The World Health Organization estimated in 2004 that 12.2% of worldwide deaths occurred as a result of ischemic heart disease. Ischemic heart disease was also deemed the leading cause of death in middle to high income countries and second only to respiratory infections in lower income countries. *The Global Burden of Disease: World Health Organization 2004 Update*, Geneva (2008). Worldwide more than 3 million people present with a ST elevation myocardial infarction (STEMI) and 4 million people present with a non-ST elevation myocardial infarction (NSTEMI) a year. White, et al., *Acute Myocardial Infarction*, Lancet 372 (9638), pp. 570-84 (August 2008).

Rates of death from ischemic heart disease have slowed or declined in most high income countries, although cardiovascular disease still accounted for 1 in 3 of all deaths in the USA in 2008. Roger, et al., *Executive summary: Heart Disease and Stroke Statistics—2012 update: A report from the American Heart Association*, Circulation 125 (1), pp. 188-97 (January 2012).

In contrast, ischemic heart disease is becoming a more common cause of death in the developing world. For example in India, ischemic heart disease had become the leading cause of death by 2004; accounting for 1.46 million deaths (14% of total deaths). Deaths in India due to ischemic heart disease were also expected to double during 1985-2015. Gupta, et al., *Epidemiology and Causation of Coronary Heart Disease and Stroke in India*, Heart 94 (1), pp. 16-26 (January 2008).

Globally, it is predicted that disability adjusted life years (DALYs) lost to ischemic heart disease will account for 5.5% of total DALYs in 2030, making it the second most important cause of disability (after unipolar depressive disorder), as well as the leading cause of death by this date.

A myocardial infarction (a common presentation of ischemic heart disease) often occurs when a coronary artery becomes occluded and can no longer supply blood to the myocardial tissue, thereby resulting in myocardial cell death. When a myocardial infarction occurs, the myocardial tissue that is no longer receiving adequate blood flow ultimately dies (without effective intervention) and is eventually replaced by scar tissue.

Within seconds of a myocardial infarction, the under-perfused myocardial cells no longer contract, leading to abnormal wall motion, high wall stresses within and surrounding the infarct, and depressed ventricular function. The high stresses at the junction between the infarcted tissue and the normal tissue lead to expansion of the infarcted area and remodeling, i.e. a cascading sequence of myocellular events, over time.

Various methods for treating a myocardial infarction are often employed. Such methods include stabilizing the hemodynamics associated with a myocardial infarction via systemic delivery of various pharmacological agents and restoring the patency of occluded vessels via thrombolytic therapy or angioplasty and stents.

Several additional methods for treating a myocardial infarction are directed to re-establishing blood flow to the ischemic area through stimulation of angiogenesis. Re-establishing blood flow at the ischemic area can, and in many instances will, reduce symptoms associated with a myocardial infarction and/or improve cardiac function.

Some methods for re-establishing blood flow and rehabilitating the heart involve invasive surgery, such as bypass surgery or angioplasty. Other methods employ lasers to bore holes through the infarctions and ischemic area(s) to promote blood flow. As one can readily appreciate, there are numerous incumbent risks associated with the noted methods.

A further method for treating a myocardial infarction is the direct or selective delivery of bioactive or pharmacological agents to the infarction and/or ischemic area (i.e. effected or damaged cardiovascular tissue). Direct delivery of a bioactive or pharmacological agent to the effected cardiovascular tissue is often preferred over the systemic delivery for several reasons. A primary reason is that a substantially greater concentration of such agents that can be delivered directly into the effected cardiovascular tissue, compared with the dilute concentrations possible through systemic delivery. Another reason is the risk of systemic toxicity which can, and in many instances will, occur with doses of pharmacological agents that are typically required to achieve desired drug concentrations in the effected cardiovascular tissue.

One common method of delivering bioactive or pharmacological agents to effected cardiovascular tissue, e.g. damaged myocardial tissue, comprises advancing a catheter through the vasculature and into the heart to inject the agents directly into the effected cardiovascular tissue from within the heart.

Another method of delivering bioactive or pharmacological agents to effected cardiovascular tissue comprises epicardial, direct injection into the tissue during an open chest procedure. The bioactive agents that can be, and have been, administered to the effected cardiovascular tissue include various pharmacological agents, such as antithrombotic agents, e.g., heparin, hirudin, and ticlopidine, and cells that are capable of maturing into actively contracting cardiac muscle cells or regenerating cardiovascular tissue. Examples of such cells include myocytes, myoblasts, mesenchymal stem cells, and pluripotent cells.

However, to date, cell therapy of effected cardiovascular tissue has not reached its full potential, due, in part, to the failure of implanted cells to survive and regenerate the damaged tissue in ischemic area(s) or regions with inadequate vascularization.

It would thus be desirable to provide bioactive and pharmacological agents (and compositions) that promote tissue survival and induce neovascularization and regeneration of effected or damaged cardiovascular tissue, and improved methods for delivering same to effected cardiovascular tissue.

It is therefore an object of the present invention to provide bioactive and pharmacological agents (and compositions) that promote tissue survival, and induce neovascularization and regeneration of damaged cardiovascular tissue.

It is another object of the present invention to provide extracellular matrix (ECM) compositions, which, when delivered to damaged biological tissue; particularly, cardiovascular tissue, induce neovascularization, host tissue proliferation, bioremodeling, and regeneration of cardiovascular tissue and associated structures with site-specific structural and functional properties.

It is yet another object of the present invention to provide improved methods and systems for administering an ECM composition directly to damaged or diseased biological tissue; particularly, cardiovascular tissue.

SUMMARY OF THE INVENTION

The present invention is directed to methods and systems for treating damaged and diseased biological tissue; particularly, cardiovascular tissue. In some embodiments, the method comprises direct delivery or administration of at least one pharmacological composition of the invention to the damaged or diseased biological tissue.

In a preferred embodiment, the pharmacological compositions comprise extracellular matrix (ECM) compositions that include at least one ECM material.

According to the invention, the ECM material can be derived from various mammalian tissue sources, including the small intestine, large intestine, stomach, lung, liver, kidney, pancreas, placenta, heart, bladder, prostate, tissue surrounding growing enamel, tissue surrounding growing bone, and any fetal tissue from any mammalian organ, and methods for preparing same.

In some embodiments, the ECM compositions further include one or more additional biologically active components to facilitate the treatment of damaged tissue and/or the tissue regenerative process.

In some embodiments, the ECM compositions thus include at least one pharmacological agent or composition, which can comprise, without limitation, antibiotics or antifungal agents, anti-viral agents, anti-pain agents, anesthetics, analgesics, steroidal anti-inflammatories, non-steroidal anti-inflammatories, anti-neoplastics, anti-spasmodics, modulators of cell-extracellular matrix interactions, proteins, hormones, enzymes and enzyme inhibitors, anticoagulants and/or anti-thrombic agents, DNA, RNA, modified DNA and RNA, NSAIDs, inhibitors of DNA, RNA or protein synthesis, polypeptides, oligonucleotides, polynucleotides, nucleoproteins, compounds modulating cell migration, compounds modulating proliferation and growth of tissue, and vasodilating agents.

In some embodiments of the invention, the pharmacological agent specifically comprises an anti-inflammatory agent or composition.

In some embodiments of the invention, the biologically active component comprises a statin. According to the invention, suitable statins include, without limitation, atorvastatin, cerivastatin, fluvastatin, lovastatin, mevastatin, pitavastatin, pravastatin, rosuvastatin, and simvastatin.

In some embodiments of the invention, the biologically active component comprises chitosan or a derivative thereof.

In some embodiments of the invention, the biologically active component comprises a cell.

In some embodiments of the invention, the biologically active component comprises a protein.

In some embodiments of the invention, the ECM compositions are formulated to facilitate injection of the ECM compositions to damaged or diseased tissue (i.e. injectable ECM compositions).

In some embodiments of the invention, one or more ECM compositions of the invention are directly administered to damaged cardiovascular tissue via a multi-needle injection system. According to the invention, the ECM compositions can be directly administered to the heart wall and/or the various cardiovascular structures associated therewith, including the epicardium, endocardium and myocardium.

BRIEF DESCRIPTION OF THE DRAWINGS

Further features and advantages will become apparent from the following and more particular description of the preferred embodiments of the invention, as illustrated in the accompanying drawings, and in which like referenced characters generally refer to the same parts or elements throughout the views, and in which.

DETAILED DESCRIPTION OF THE PREFERRED EMBODIMENT

Before describing the present invention in detail, it is to be understood that this invention is not limited to particularly exemplified apparatus, systems, compositions or methods as such may, of course, vary. Thus, although a number of systems, compositions and methods similar or equivalent to those described herein can be used in the practice of the present invention, the preferred systems, compositions and methods are described herein.

It is also to be understood that, although the systems, pharmacological compositions and methods of the invention are illustrated and described in connection with administration (or delivery) of pharmacological compositions (and bioactive and pharmacological agents) to cardiovascular tissue, the systems, compositions and methods of the invention are not limited to such delivery. According to the invention, the systems and methods of the invention can be employed to administer pharmacological compositions (and bioactive and pharmacological agents) to numerous additional biological tissue, including, without limitation, gastrointestinal and respiratory organ tissue.

It is also to be understood that, although a preferred method of delivering a pharmacological composition of the invention to biological tissue comprises direct injection into the tissue. The delivery of the pharmacological composition is not limited to direct injection. According to the invention, a pharmacological composition of the invention can be delivered to biological tissue by other conventional means, including topical administration.

It is further to be understood that the terminology used herein is for the purpose of describing particular embodiments of the invention only and is not intended to be limiting.

Unless defined otherwise, all technical and scientific terms used herein have the same meaning as commonly understood by one having ordinary skill in the art to which the invention pertains.

Further, all publications, patents and patent applications cited herein, whether supra or infra, are hereby incorporated by reference in their entirety.

Finally, as used in this specification and the appended claims, the singular forms "a," "an" and "the" include plural referents unless the content clearly dictates otherwise. Thus, for example, reference to "an anti-inflammatory" includes two or more such agents and the like.

DEFINITIONS

The terms "cardiac tissue damage", "cardiac tissue injury" and "cardiovascular tissue damage" are used interchangeably herein, and mean and include any area of abnormal tissue in the cardiovascular system or heart caused by a disease, disorder, injury or damage, including damage to the epicardium, endocardium and/or myocardium. Non-limiting examples of causes of cardiovascular tissue damage include acute or chronic stress (systemic hypertension, pulmonary hypertension, valve dysfunction, etc.), coronary artery disease, ischemia or infarction, inflammatory disease and cardiomyopathies.

As is well known in the art, cardiovascular tissue damage most often involves damage or injury to the myocardium and, therefore, for the purposes of this disclosure, myocardial damage or injury is equivalent to cardiovascular tissue damage.

The term "damaged tissue", as used herein, means and includes biological tissue; particularly, cardiovascular tissue damaged or injured by trauma, ischemic tissue, infarcted tissue or tissue damaged by any means which results in interruption of normal blood flow to the tissue.

The terms "prevent" and "preventing" are used interchangeably herein, and mean and include reducing the frequency or severity of a disease, condition or disorder. The term does not require an absolute preclusion of the disease, condition or disorder. Rather, this term includes decreasing the chance for disease occurrence.

The terms "treat" and "treatment" are used interchangeably herein, and mean and include medical management of a patient with the intent to cure, ameliorate, stabilize, or prevent a disease, pathological condition or disorder. The terms include "active treatment", i.e. treatment directed specifically toward the improvement of a disease, pathological condition or disorder, and "causal treatment", i.e. treatment directed toward removal of the cause of the associated disease, pathological condition or disorder.

The terms "treat" and "treatment" further include "palliative treatment", i.e. treatment designed for the relief of symptoms rather than the curing of the disease, pathological condition or disorder, "preventative treatment", i.e. treatment directed to minimizing or partially or completely inhibiting the development of the associated disease, pathological condition or disorder, and "supportive treatment", i.e. treatment employed to supplement another specific therapy directed toward the improvement of the associated disease, pathological condition or disorder.

The term "chamber remodeling", as used herein, means and includes a series of events (which may include changes in gene expression, molecular, cellular and interstitial changes) that result in changes in size, shape and function of cardiac tissue following stress or injury. As is well known in the art, remodeling can occur after a myocardial infarction, pressure overload (e.g., aortic stenosis, hypertension), volume overload (e.g., valvular regurgitation), inflammatory heart disease (e.g., myocarditis), or in idiopathic cases (e.g., idiopathic dilated cardiomyopathy).

The term "angiogenesis", as used herein, means a physiologic process involving the growth of new blood vessels from pre-existing blood vessels.

The term "neovascularization", as used herein, means and includes the formation of functional vascular networks that can be perfused by blood or blood components. Neovascularization includes angiogenesis, budding angiogenesis, intussuceptive angiogenesis, sprouting angiogenesis, therapeutic angiogenesis and vasculogenesis.

The terms "extracellular matrix", "extracellular matrix material" and "ECM material" are used interchangeably herein, and mean a collagen-rich substance that is found in between cells in animal tissue and serves as a structural element in tissues. It typically comprises a complex mixture of polysaccharides and proteins secreted by cells. The extracellular matrix can be isolated and treated in a variety of ways. Extracellular matrix material (ECM) can be isolated from small intestine submucosa, stomach submucosa, urinary bladder submucosa, tissue mucosa, dura mater, liver basement membrane, pericardium or other tissues. Following isolation and treatment, it is commonly referred to as extracellular matrix or ECM material.

The terms "pharmacological agent", "pharmaceutical agent", "agent", "active agent", "drug" and "active agent formulation" are used interchangeably herein, and mean and include an agent, drug, compound, composition of matter or mixture thereof, including its formulation, which provides some therapeutic, often beneficial, effect. This includes any physiologically or pharmacologically active substance that produces a localized or systemic effect or effects in animals, including warm blooded mammals, humans and primates; avians; domestic household or farm animals, such as cats, dogs, sheep, goats, cattle, horses and pigs; laboratory animals, such as mice, rats and guinea pigs; fish; reptiles; zoo and wild animals; and the like.

The terms "pharmacological agent", "pharmaceutical agent", "agent", "active agent", "drug" and "active agent formulation" thus mean and include, without limitation, antibiotics, anti-viral agents, analgesics, steroidal anti-inflammatories, non-steroidal anti-inflammatories, anti-neoplastics, anti-spasmodics, modulators of cell-extracellular matrix interactions, proteins, hormones, enzymes and enzyme inhibitors, anticoagulants and/or antithrombic agents, DNA, RNA, modified DNA and RNA, NSAIDs, inhibitors of DNA, RNA or protein synthesis, polypeptides, oligonucleotides, polynucleotides, nucleoproteins, compounds modulating cell migration, compounds modulating proliferation and growth of tissue, and vasodilating agents.

The terms "anti-inflammatory" and "anti-inflammatory agent" are also used interchangeably herein, and mean and include a "pharmacological agent" and/or "active agent formulation", which, when a therapeutically effective amount is administered to a subject, prevents or treats bodily tissue inflammation i.e. the protective tissue response to injury or destruction of tissues, which serves to destroy, dilute, or wall off both the injurious agent and the injured tissues. Anti-inflammatory agents thus include, without limitation, alclofenac, alclometasone dipropionate, algestone acetonide, alpha amylase, amcinafal, amcinafide, amfenac sodium, amiprilose hydrochloride, anakinra, anirolac, anitrazafen, apazone, balsalazide disodium, bendazac, benoxaprofen, benzydamine hydrochloride, bromelains, broperamole, budesonide, carprofen, cicloprofen, cintazone, cliprofen, clobetasol propionate, clobetasone butyrate, clopirac, cloticasone propionate, cormethasone acetate, cortodoxone, decanoate, deflazacort, delatestryl, depo-testosterone, desonide, desoximetasone, dexamethasone dipropionate, diclofenac potassium, diclofenac sodium, diflorasone diacetate, diflumidone sodium, diflunisal, difluprednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halcinonide, halobetasol propionate, halopredone acetate, ibufenac, ibuprofen, ibuprofen aluminum, ibuprofen piconol, ilonidap, indomethacin, indomethacin sodium, indoprofen, indoxole, intrazole, isoflupredone acetate, isoxepac, isoxicam, ketoprofen, lofemizole hydrochloride, lomoxicam, loteprednol etabonate, meclofenamate sodium, meclofenamic acid, meclorisone dibutyrate, mefenamic acid, mesalamine, meseclazone, mesterolone, methandrostenolone, methenolone, methenolone acetate, methylprednisolone suleptanate, momiflumate, nabumetone, nandrolone, naproxen, naproxen sodium, naproxol, nimazone, olsalazine sodium, orgotein, orpanoxin, oxandrolane, oxaprozin, oxyphenbutazone, oxymetholone, paranyline hydrochloride, pentosan polysulfate sodium, phenbutazone sodium glycerate, pirfenidone, piroxicam, piroxicam cinnamate, piroxicam olamine, pirprofen, prednazate, prifelone, prodolic acid, proquazone, proxazole, proxazole citrate, rimexolone, romazarit, salcolex, salnacedin, salsalate, sanguinarium chloride, seclazone, sermetacin, stanozolol, sudoxicam, sulindac, suprofen, talmetacin, talniflumate, talosalate, tebufelone, tenidap, tenidap sodium, tenoxicam, tesicam, tesimide, testosterone, testosterone blends, tetrydamine, tiopinac, tixocortol pivalate, tolmetin, tolmetin sodium, triclonide, triflumidate, zidometacin, and zomepirac sodium.

The term "chitosan", as used herein, means and includes the family of linear polysaccharides consisting of varying amounts of β (1→4) linked residues of N-acetyl-2 amino-2-deoxy-D-glucose and 2-amino-2-deoxy-Dglucose residues, and all derivatives thereof.

The terms "active agent formulation", "pharmacological agent formulation" and "agent formulation", are also used interchangeably herein, and mean and include an active agent (and chitosan) optionally in combination with one or more pharmaceutically acceptable carriers and/or additional inert ingredients. According to the invention, the formulations can be either in solution or in suspension in the carrier.

The term "pharmacological composition", as used herein, means and includes a composition comprising a "pharmacological agent" and/or an "extracellular matrix material" and/or a "pharmacological agent formulation" and/or any additional agent or component identified herein.

The term "therapeutically effective", as used herein, means that the amount of the "pharmacological composition" and/or "pharmacological agent" and/or "active agent formulation" administered is of sufficient quantity to ameliorate one or more causes, symptoms, or sequelae of a disease or disorder. Such amelioration only requires a reduction or alteration, not necessarily elimination, of the cause, symptom, or sequelae of a disease or disorder.

The terms "delivery" and "administration" are used interchangeably herein, and mean and include providing a "pharmacological composition" or "pharmacological agent" or "active agent formulation" to a treatment site, e.g., damaged tissue, through any method appropriate to deliver the functional agent or formulation or composition to the treatment site. Non-limiting examples of delivery methods include direct injection, percutaneous delivery and topical application at the treatment site.

The term "percutaneous", as used herein, means and includes any penetration through the skin of a patient or subject, whether in the form of a small cut, incision, hole, cannula, tubular access sleeve or port or the like.

The terms "patient" and "subject" are used interchangeably herein, and mean and include warm blooded mammals, humans and primates; avians; domestic household or farm animals, such as cats, dogs, sheep, goats, cattle, horses and pigs; laboratory animals, such as mice, rats and guinea pigs; fish; reptiles; zoo and wild animals; and the like.

The term "comprise" and variations of the term, such as "comprising" and "comprises," means "including, but not limited to" and is not intended to exclude, for example, other additives, components, integers or steps.

The following disclosure is provided to further explain in an enabling fashion the best modes of performing one or more embodiments of the present invention. The disclosure is further offered to enhance an understanding and appreciation for the inventive principles and advantages thereof, rather than to limit in any manner the invention. The invention is defined solely by the appended claims including any amendments made during the pendency of this application and all equivalents of those claims as issued.

As will readily be appreciated by one having ordinary skill in the art, the present invention substantially reduces or eliminates the disadvantages and drawbacks associated with prior art methods of treating damaged or diseased biological tissue.

In overview, the present disclosure is directed to methods and systems for treating damaged and diseased biological tissue; particularly, cardiovascular tissue, via the "direct" delivery of a pharmacological composition (and/or pharmacological agent and/or formulation) to the damaged or diseased tissue. According to the invention, the delivery of a therapeutically effective amount of a pharmacological composition of the invention to damaged or diseased tissue induces neovascularization, host tissue proliferation, bioremodeling and regeneration of new tissue.

According to the invention, the pharmacological compositions can comprise mixed liquids, mixed emulsions, mixed gels, mixed pastes, or mixed solid particulates.

Figure 3A:
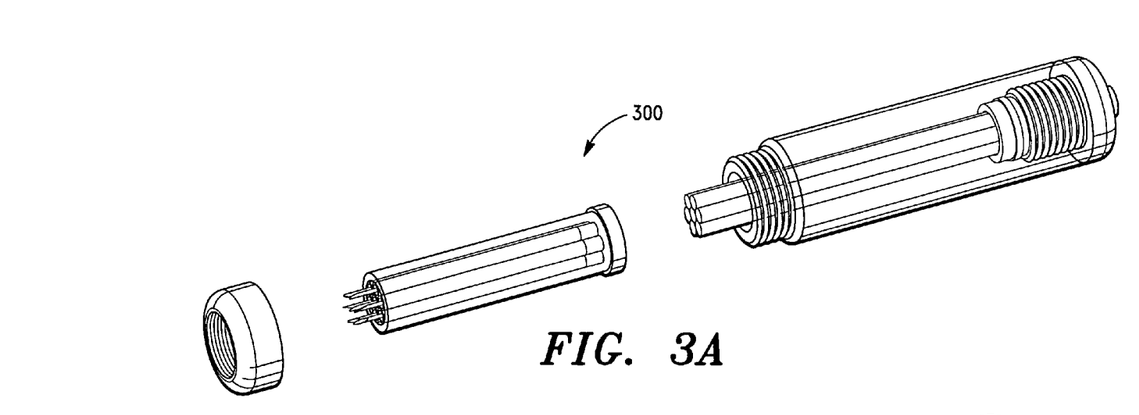
FIG. 3A is an exploded perspective view of one embodiment of a multi-needle injection apparatus that is suitable for direct administration of ECM compositions to biological tissue, e.g. cardiovascular tissue, in accordance with the invention.
Figure 3B:
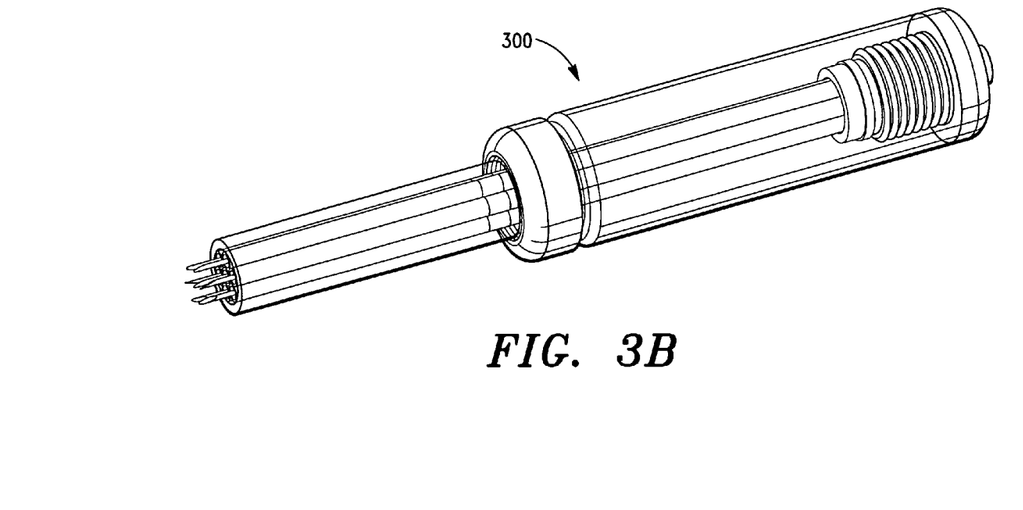
FIG. 3B is an assembled perspective view of the multi-needle injection apparatus shown in FIG. 3A, in accordance with the invention.

In some embodiments, one or more pharmacological compositions of the invention are directly administered to the damaged or diseased tissue via a multi-needle injection system, such as disclosed in Co-pending Application No. 61/704,634, filed Sep. 24, 2012 and illustrated in FIGS. 3A and 3B.

In a preferred embodiment, the pharmacological compositions comprise extracellular matrix (ECM) compositions that include at least one extracellular matrix (hereinafter "ECM material").

According to the invention, the ECM material can be derived from various mammalian tissue sources and methods for preparing same, such as disclosed in U.S. Pat. Nos. 7,550,004, 7,244,444, 6,379,710, 6,358,284, 6,206,931, 5,733,337 and 4,902,508 and U.S. application Ser. No. 12/707,427; which are incorporated by reference herein in their entirety. The mammalian tissue sources include, without limitation, the small intestine, large intestine, stomach, lung, liver, kidney, pancreas, placenta, heart, bladder, prostate, tissue surrounding growing enamel, tissue surrounding growing bone, and any fetal tissue from any mammalian organ.

As is well known in the art, the urinary bladder submucosa is an extracellular matrix that has the tunica mucosa (which includes the transitional epithelial layer and the tunica propria), a submucosal layer, three layers of muscularis, and the adventitia (a loose connective tissue layer). This general configuration is true also for small intestine submucosa (SIS) and stomach submucosa (SS).

Other tissues, such as the liver and pancreas have ECM material called basement membrane. Basement membrane generally does not demonstrate the kind of tensile strength found in submucosa. However, other useful properties may be opportunistically employed from the ECM material of such tissues as the liver, pancreas, placenta and lung tissues; all of which have either a basement membrane or interstitial membrane (as with the lung). For example, pancreatic extracellular membrane supports beta islet cells that are critical to pancreatic function. Also, for example, the liver is one tissue known to be able to regenerate itself and therefore special qualities may be present in the liver basement membrane that help facilitate that process. The ECM material surrounding developing tooth enamel and developing bone also have particular advantages over other matrices in that they support the growth and differentiation of the hard tissues of bone and enamel.

According to the invention, the ECM material can be used in whole or in part, so that, for example, an ECM material can contain just the basement membrane (or transitional epithelial layer) with the subadjacent tunica propria, the tunica submucosa, tunica muscularis, and tunica serosa. The ECM material component of the composition can contain any or all of these layers, and thus could conceivably contain only the basement membrane portion, excluding the submucosa. However, generally, and especially since the submucosa is thought to contain and support the active growth factors and other proteins necessary for in vivo tissue regeneration, the ECM or matrix composition from any given source will contain the active extracellular matrix portions that support cell development and differentiation and tissue regeneration.

For purposes of this invention, the ECM material from any of the mammalian tissue consists of several basically inseparable layers broadly termed ECM material. For example, where it is thought that separating a basement membrane from the submucosa is considered to be very difficult, if not impossible, because the layers are thin and it is not possible to delaminate them from each other, the ECM material from that particular layer will probably necessarily contain some basement membrane with the submucosa.

According to the invention, the ECM material can be formed into a particulate and fluidized, as described in U.S. Pat. Nos. 5,275,826, 6,579,538 and 6,933,326, to form an ECM composition of the invention.

According to the invention, various conventional means can be employed to form a particulate ECM material. In some embodiments, the ECM material is formed into a sheet, fluidized (or hydrated), if necessary, frozen and ground.

In some embodiments of the invention, the ground ECM material is subsequently filtered to achieve a desired particulate size. Thus, in some embodiments, the ECM material has a particulate size no greater than 2000 microns. In some embodiments, the ECM material preferably has a particulate size no greater than 500 microns. In a preferred embodiment, the ECM material has a particulate size in the range of about 20 microns to about 300 microns.

According to the invention, fluidized or emulsified compositions (the liquid or semi-solid forms) can comprise various certain concentrations of ECM material. In some embodiments of the invention, the concentration of the ECM material is greater than about 5%, more preferably, greater than about 20%, even more preferably, greater than about 70%.

According to the invention, the particulate ECM material can be fluidized or hydrated by various conventional buffer materials. Suitable buffer materials include, without limitation, water and saline.

According to the invention, the ECM compositions of the invention can also comprise ECM material from two or more mammalian sources. Thus, for example, the composition can comprise ECM material combinations from such sources as, for example, but not limited to, small intestine submucosa, liver basement membrane, stomach submucosa, urinary bladder submucosa, placental basement membrane, pancreatic basement membrane, large intestine submucosa, lung interstitial membrane, respiratory tract submucosa, heart ECM material, dermal matrix, and, in general, ECM material from any mammalian fetal tissue. The ECM material sources can also comprise different mammalian animals or an entirely different species of mammals.

The ECM composition can thus comprise ECM material from three mammalian tissue sources, four mammalian tissue sources, five mammalian tissue sources, six mammalian tissue sources, and conceivably up to ten or more tissue sources. The tissue sources can be from the same mammal (for example the same cow, the same pig, the same rodent, the same human, etc.), the same species of mammal (e.g. cow, pig, rodent, human), or different mammalian animals, but the same species, (e.g. cow 1 and cow 2, or pig 1 and pig 2), or different species of mammals (for example liver matrix from a pig, small intestine submucosa from a cow, and urinary bladder submucosa from a dog, all mixed together in the composition).

According to the invention, any one of the noted tissue sources can provide material that can be formulated (or processed) into a desired form (liquid, semi-solid or solid form), for use in an ECM composition of the invention.

According to the invention, the liquid or semi-solid components of the ECM compositions (i.e. liquids, gels, emulsions or pastes) can comprise various concentrations. Preferably, the concentration of the liquid or semi-solid components of the ECM compositions are in the range of about 0.001 mg/ml to about 200 mg/ml. Suitable concentration ranges thus include, without limitation: about 5 mg/ml to about 150 mg/ml, about 10 mg/ml to about 125 mg/ml, about 25 mg/ml to about 100 mg/ml, about 20 mg/ml to about 75 mg/ml, about 25 mg/ml to about 60 mg/ml, about 30 mg/ml to about 50 mg/ml, and about 35 mg/ml to about 45 mg/ml and about 40 mg/ml. to about 42 mg/ml.

The noted concentration ranges are, however, merely exemplary and not intended to be exhaustive or limiting. It is understood that any value within any of the listed ranges is deemed a reasonable and useful value for a concentration of a liquid or semi-solid component of an ECM composition.

According to the invention, the dry particulate or reconstituted particulate that forms a gel emulsion or paste of the two ECM materials can also be mixed together in various proportions. For example, the particulates can comprise 50% of small intestine submucosa mixed with 50% of pancreatic basement membrane. The mixture can then similarly be fluidized by hydrating in a suitable buffer, such as saline.

As indicated above, in some embodiments of the invention, the ECM compositions are formulated to be injected into damaged or cardiovascular tissue, i.e. injectable ECM compositions. In some embodiments of the invention, the injectable ECM compositions thus comprise approximately 70% particulate ECM material and approximately 30% fully hydrolyzed ECM gel.

According to the invention, the pharmacological compositions of the invention can further include one or more additional bioactive agents or components to aid in the treatment of damaged tissue and/or facilitate the tissue regenerative process.

In some embodiments, the pharmacological compositions of the invention thus include at least one pharmacological agent or composition, which can comprise, without limitation, antibiotics or antifungal agents, anti-viral agents, anti-pain agents, anesthetics, analgesics, steroidal anti-inflammatories, non-steroidal anti-inflammatories, anti-neoplastics, anti-spasmodics, modulators of cell-extracellular matrix interactions, proteins, hormones, enzymes and enzyme inhibitors, anticoagulants and/or antithrombic agents, DNA, RNA, modified DNA and RNA, NSAIDs, inhibitors of DNA, RNA or protein synthesis, polypeptides, oligonucleotides, polynucleotides, nucleoproteins, compounds modulating cell migration, compounds modulating proliferation and growth of tissue, and vasodilating agents.

Suitable pharmacological agents and/or compositions thus include, without limitation, atropine, tropicamide, dexamethasone, dexamethasone phosphate, betamethasone, betamethasone phosphate, prednisolone, triamcinolone, triamcinolone acetonide, fluocinolone acetonide, anecortave acetate, budesonide, cyclosporine, FK-506, rapamycin, ruboxistaurin, midostaurin, flurbiprofen, suprofen, ketoprofen, diclofenac, ketorolac, nepafenac, lidocaine, neomycin, polymyxin b, bacitracin, gramicidin, gentamicin, oyxtetracycline, ciprofloxacin, ofloxacin, tobramycin, amikacin, vancomycin, cefazolin, ticarcillin, chloramphenicol, miconazole, itraconazole, trifluridine, vidarabine, ganciclovir, acyclovir, cidofovir, ara-amp, foscarnet, idoxuridine, adefovir dipivoxil, methotrexate, carboplatin, phenylephrine, epinephrine, dipivefrin, timolol, 6-hydroxydopamine, betaxolol, pilocarpine, carbachol, physostigmine, demecarium, dorzolamide, brinzolamide, latanoprost, sodium hyaluronate, insulin, verteporfin, pegaptanib, ranibizumab, and other antibodies, antineoplastics, AntiVGEFs, ciliary neurotrophic factor, brain-derived neurotrophic factor, bFGF, Caspase-1 inhibitors, Caspase-3 inhibitors, α-Adrenoceptors agonists, NMDA antagonists, Glial cell line-derived neurotrophic factors (GDNF), pigment epithelium-derived factor (PEDF), and NT-3, NT-4, NGF, IGF-2.

According to the invention, the amount of a pharmacological agent added to an ECM composition of the invention will, of course, vary from agent to agent. For example, in one embodiment, wherein the pharmacological agent comprises dicloflenac (Voltaren®), the amount of dicloflenac included in the ECM composition is preferably in the range of 10 µg-75 mg.

In some embodiments of the invention, the pharmacological agent specifically comprises an anti-inflammatory agent. According to the invention, suitable anti-inflammatory agents include, without limitation, alclofenac, alclometasone dipropionate, algestone acetonide, alpha amylase, amcinafal, amcinafide, amfenac sodium, amiprilose hydrochloride, anakinra, anirolac, anitrazafen, apazone, balsalazide disodium, bendazac, benoxaprofen, benzydamine hydrochloride, bromelains, broperamole, budesonide, carprofen, ciclopro-fen, cintazone, cliprofen, clobetasol propionate, clobetasone butyrate, clopirac, cloticasone propionate, cormethasone acetate, cortodoxone, decanoate, deflazacort, delatestryl, depo-testosterone, desonide, desoximetasone, dexamethasone dipropionate, diclofenac potassium, diclofenac sodium, diflorasone diacetate, diflumidone sodium, diflunisal, difluprednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halcinonide, halobetasol propionate, halopredone acetate, ibufenac, ibuprofen, ibuprofen aluminum, ibuprofen piconol, ilonidap, indomethacin, indomethacin sodium, indoprofen, indoxole, intrazole, isoflupredone acetate, isoxepac, isoxicam, ketoprofen, lofemizole hydrochloride, lomoxicam, loteprednol etabonate, meclofenamate sodium, meclofenamic acid, meclorisone dibutyrate, mefenamic acid, mesalamine, meseclazone, mesterolone, methandrostenolone, methenolone, methenolone acetate, methylprednisolone suleptanate, momiflumate, nabumetone, nandrolone, naproxen, naproxen sodium, naproxol, nimazone, olsalazine sodium, orgotein, orpanoxin, oxandrolane, oxaprozin, oxyphenbutazone, oxymetholone, paranyline hydrochloride, pentosan polysulfate sodium, phenbutazone sodium glycerate, pirfenidone, piroxicam, piroxicam cinnamate, piroxicam olamine, pirprofen, prednazate, prifelone, prodolic acid, proquazone, proxazole, proxazole citrate, rimexolone, romazarit, salcolex, salnacedin, salsalate, sanguinarium chloride, seclazone, sermetacin, stanozolol, sudoxicam, sulindac, suprofen, talmetacin, talniflumate, talosalate, tebufelone, tenidap, tenidap sodium, tenoxicam, tesicam, tesimide, testosterone, testosterone blends, tetrydamine, tiopinac, tixocortol pivalate, tolmetin, tolmetin sodium, triclonide, triflumidate, zidometacin, and zomepirac sodium.

According to the invention, the amount of an anti-inflammatory added to an ECM composition of the invention can similarly vary from anti-inflammatory to anti-inflammatory. For example, in one embodiment of the invention, wherein the pharmacological agent comprises ibuprofen (Advil®), the amount of ibuprofen included in the ECM composition is preferably in the range of 100 µg-200 µg.

In some embodiments of the invention, the pharmacological agent comprises a statin, i.e. a HMG-CoA reductase inhibitor. According to the invention, suitable statins include, without limitation, atorvastatin (LIPITOR®), cerivastatin, fluvastatin (Lescol®), lovastatin (Mevacor®, Altocor®, Altoprev®), mevastatin, pitavastatin (Livalo®, Pitava®), pravastatin (Pravachol®, Selektine®, Lipostat®), rosuvastatin (Crestor®), and simvastatin (Zocor®, Lipex®). Several actives comprising a combination of a statin and another agent, such as ezetimbe/simvastatin (Vytorin®), are also suitable.

Applicant has found that statins exhibit numerous beneficial properties that provide several beneficial biochemical actions or activities. The properties and beneficial actions resulting therefrom are discussed in detail below.

Anticholesterolemic Properties/Actions

As is well known in the art, statins are a class of drugs that primarily function to lower levels of cholesterol production in the liver. Lower levels of cholesterol are achieved via the statins limiting the production of mevalonate in the cholestrol biosynthetic pathway. Statins competitively inhibit HMG-CoA reductase, which, because the molecules are so similar, results in the statins actually taking the place of the HMG-CoA reductase in the cholesterol biosynthetic pathway and reducing the rate at which the mevalonate is produced, subsequently lowering the rate at which cholesterol is produced in the liver.

Anti-Inflammatory Properties/Actions

Statins also have numerous additional favorable effects on the vascular wall cells, and cardiovascular system. One specific example of this is thromboxane A2 ($TXA_2$). Statins can aid in the reduction of $TXA_2$, which then lowers the platelet activation in the cardiovascular system.

$TXA_2$ is also known as a vasoconstrictor and is especially important during tissue injury and inflammation due to its impact on platelet activation and aggregation, as well as its ability to augment the expression of adhesion molecules and chemokines. This allows statins to aid in the reduction of inflammation by the reduction of $TXA_2$, which results in less vascoconstriction, less platelet activation and aggregation, as well as reduced augmentation of adhesion molecules and chemokines.

Statins further impact vascular wall cells and the cardiovascular system by blocking ras homilog gene family, member A (RhoA) activation. Blocking RhoA activation further impacts numerous systems, such as macrophage growth, tissue plasminogen activators (t-PA), plasminogen activator inhibitor type 1 (PAI-1), smooth muscle cell (SMC) proliferation, nitric oxide (NO) production, endothelins, and angiotensin receptors. When statins block RhoA activation, the resultant impact can be seen in many phsyiological responses of the cardiovascular system, including vascular inflammation, smooth muscle cell production and size, and vasconstriction inter alia.

Macrophage growth reduced by blocking RhoA activation results in the reduction of matrix metalloprotinases (MMPs) and tissue factors (TF). MMPs are part of a larger family of metalloprotinase enzymes that play on important part in wound healing and inflammation. MMPs are produced by activated neutrophils and macrophages (inflammatory cells).

Statins facilitate the reduction of inflammatory factors by lowering macrophage growth, which results in reduced production of MMPs. Lowered MMPs also results in a lowered presence of thrombi as the MMPs attach to ECM present in thrombi or damaged ECM at wound sites. Macrophage growth reduction also results in lowered presence of tissue factor (TF).

TF is a protein necessary for the initiation of thrombin formation. This factor also enables cells to initiate the coagulation cascade. Lowered presence of TF results in lowered presence of thrombi in the cardiovascular system, especially in conjunction with reduced MMPs.

Plaque Stabilizing Properties/Actions

Reduced MMPs and reduced TF also results in increased plaque stability which can help to prevent stroke or myocardial infarction by reducing the probability of a portion of the plaque to break off and become lodged within a smaller vessel. Plaque stability further aids in reduction of atherosclerosis.

Fibrinolysis Properties/Actions

Blocking RhoA activation also affects the presence of tissue plasminogen activators (t-PA) and plasminogen activator inhibitor type 1 (PAI-1). T-PA is a protein involved in the breakdown of blood clots, and is found on endothelial cells. As an enzyme it catalyzes the conversion of plasminogen to plasmin, the major enzyme responsible for clot breakdown (fibrinolysis).

PAI-1 is a protein that functions as the principal inhibitor oft-PA. Thus, PAI-1 is the principal inhibitor of fibrinolysis. With t-PA presence raised and PAI-1 diminished from the blocking of RhoA activation caused by statins, a reduced thrombotic effect is realized due to reduced opportunity for fibrin to form the polymeric mesh of a hemostatic plug. The reduced MMPs and TF that result from the use of statins work in concert with the increased t-PA and reduced PAI-1 to further reduce the potential for thrombii.

NO Regulation Properties/Actions

Blocking RhoA activation also affects the presence of Nitric Oxide (NO) in the cardiovascular system. The endothelium uses NO to signal the surrounding smooth muscles to relax, resulting in vasodialation and increased blood flow. NO contributes to vessel homeostasis by inhibiting vascular smooth muscle contraction and growth, platelet aggregation, and leukocyte adhesion to the endothelium. These factors are what allow NO to aid in the reduction of endothelial dysfunction when modulated in such a way as is typical with the administration of statins. The reduction of leukocyte adhesion is a specific example of how the NO production associated with statins aids in the reduction inflammation desired when coadministered locally with an extracellular matrix.

RhoA Activation Blocking Properties/Actions

The administration of statins can affect the presence of endothelins and agiotensin receptors. Endothelins and angiotensin receptors can also be affected by the subsequent blocking of RhoA activation associated with statin administration.

Endothelins are proteins that constrict blood vessels and raise blood pressure. There are three isoforms; ET-1, ET-2, and ET-3, with ET-1 being the isoform primarily affected by statins and RhoA activation blocking. Secretion of ET-1 from the endothelium signals vasoconstriction and influences local cellular growth and survival. ET-1 has been implicated in the development and progression of vascular disorders, such as atherosclerosis and hypertension. The decrease in the presence of ET-1 associated with statins and RhoA activation blocking results in decreased vasoconstriction and progression of the aforementioned vascular disorders.

Angiotensin receptors are protein coupled receptors that are responsible for the signal transduction of the vasoconstricting stimulus of the main effector hormone angiotensin II. Angiotensin Receptor II Type I (AT-1) is the angiotensin receptor primarily affected by statin administration and RhoA activation blocking. AT-1 mediates vasocontraction, cardiac hypertrophy, vascular smooth muscle cell proliferation, inter alia. The reduction in AT-1 that accompanies statin administration and RhoA activation blocking results in reduced vasoconstriction in the cardiovascular system.

C-Reactive Protein Reduction Properties/Actions

C-Reactive Proteins (CRP) are also influenced by statin administration. CRP are found in the blood; the levels of which deviate in response to differing levels of inflammation. CRP levels diminish in response to statin administration. This functions as a result of a statin's impact on the reduction of inflammation.

Adhesion Molecule Reduction Properties/Actions

Adhesion molecules are proteins that are located on the cell surface and are involved with inflammation and thrombin formation in vascular endothelial cells. With higher incidence of inflammation comes higher incidence of cell adhesion molecules. A statin functions to reduce the presence of adhesion molecules on the endothelium. This helps to reduce inflammation by removing the attachment mechanism for leukocytes and subsequent plaque buildup, the result being lowered chance for atherosclerosis.

Rac-1 Reduction Properties/Actions

Rac-1 is a protein found in human cells. It plays a central role in endothelial cell migration, tubulogenesis, adhesion, and permeability. The expression of Rac-1 can be affected by the administration of statins, specifically such that Rac-1 is decreased by statins. The decrease in the presence of Rac-1 also results in the decrease of reactive oxygen species (ROS). ROS are chemically reactive molecules that have important roles in cell signaling and homeostasis.

Given the benefits of statins on the cardiovascular system; particularly, the effects on inflammation within the cardiovascular system, Applicant has found great benefit from administration of ECM material to cardiovascular tissue, wherein the ECM material is impregnated, coated, covered, or otherwise in contact with statins.

Typical systemic administrations of statins range from 10 mg-80 mg daily. However, it is well known in the art that, in some instances, the dosage of a statin that is required to reach a therapeutically effective local level can result in various toxicities within different organ systems, such as the liver and musculature. However, due to the direct nature of the administration of statins when incorporated in or provided in contact with an ECM material or composition of the invention, therapeutically effective dosages can be much smaller, thereby, substantially reducing the possibility of systemic toxicities.

According to the invention, the amount of a statin added to a pharmacological composition of the invention is preferably less than 20 mg, more preferably, less than approximately 10 mg.

In some embodiments of the invention, the ECM material includes 100 µg-5 mg of a statin. In some embodiments of the invention, the ECM material includes 500 µg-2 mg of a statin.

In some embodiments of the invention, the bioactive agent comprises chitosan or a derivative thereof.

Chitosan exhibits a wide range of favorable biochemical properties that make it an outstanding agent for use in the medical field. The biochemical properties of chitosan, which is discussed below, include biocompatibility, biodegradability and non-toxicity. Additional properties, such as analgesic, hemostatic, antimicrobial, and antioxidant have also been reported. See Aranaz, et al., *Functional Characterization of Chitin and Chitosan*, Current Chemical Biology, vol. 3, pp. 203-230 (2009); and Kumar MNVR, *A Review of Chitin and Chitosan Applications*, React. Funct. Polm., vol. 46, pp. 1-27 (2000).

As is well known in the art, chitin and chitosan are typically described as a family of linear polysaccharides consisting of varying amounts of β (1→4) linked residues of N-acetyl-2 amino-2-deoxy-D-glucose (denoted hereafter as A residues) and 2-amino-2-deoxy-Dglucose residues (denoted hereafter as D residues).

Chitin samples have a low amount of D units and hence the polymer is insoluble in acidic aqueous media. On the other hand, the amount of D units in chitosan samples is high enough to allow the polymer to dissolve in acidic aqueous media. Some authors consider chitosan to be the polymer with at least 60% of D residues. See S. Aiba, *Studies on Chitosan: 4. Lysozymic Hydrolysis of Partially N-Acetylated Chitosans*, J. Biol. Macromol., vol. 14(4), pp. 225-228 (1992).

Chitin is the second most abundant natural polymer in nature after cellulose and it is found in the structure of a wide number of invertebrates (crustaceans' exoskeleton, insects' cuticles) and the cell walls of fungi, among others. On the other hand, chitosan only occurs naturally in some fungi (*Mucoraceae*).

Chitosan is prepared by hydrolysis of acetamide groups of chitin. This is normally conducted by severe alkaline hydrolysis treatment due to the resistance of such groups imposed by the trans arrangement of the C2-C3 substituents in the sugar ring.

As stated and discussed in detail below, chitosan exhibits a wide range of favorable biochemical properties that make it an outstanding agent for use in the medical field.

Biodegradability Properties/Actions

Although chitosan is absent from mammals, chitosan can be readily degraded in vivo by several proteases (lysozyme, papain, pepsin . . . ). It has also been found that the biodegradation of chitosan leads to the release of non-toxic oligosaccharides of variable length, which can be subsequently incorporated to glycosaminoglycans and glycoproteins, to metabolic pathways or be excreted. See Pangburn, et al., *Lysozyme Degradation of Partially Deacetylated Chitin, its Films and Hydrogels*, vol. 3(2), pp. 105-108 (1982).

Biocompatibility Properties/Actions

Chitosan also exhibits very good compatibility; particularly, cytocompatibility. The enhanced cytocompatibility of chitosan has been proven in vitro with myocardial, endothelial and epithellial cells, fibroblast, hepatocytes, condrocytes and keratinocytes. See Chatelet, et al., *Influence of the Degree of Acetylation on Some Biological Properties of Chitosan Films*, Biomaterials, vol. 22(3), pp. 261-268 (2001).

Analgesic Properties/Actions

It has been reported that chitosan exhibits very favorable analgesic properties (or effects). Okamoto, et al. specifically studied the analgesic effect of chitosan on inflammatory pain due to intraperitoneal administration of acetic acid. See Okamoto, et al., *Analgesic Effects of Chitin and Chitosan*, Carbohyd. Poly., vol. 49, pp. 249-252 (2002).

Okamoto, et al. found that, due to its polycationic nature, the free primary amino groups of chitosan can protonate in the presence of proton ions and, thereby, reduce the pH, which is a primary cause of the analgesic properties. From experimental data, it was also concluded that the analgesic effect was due primarily to the absorption of bradykinin, one of the main components (or substances) related to pain.

Haemostatic Properties/Actions

It has also been reported that chitosan, as well as sulphated chitosan oligomers, exhibits anticoagulant activity tested in vitro. The anticoagulant activity of chitosan is deemed to be related to its positive charge, since red blood cells' membranes are negatively charged. See Rao, et al., *Use of Chitosan as Biomaterial: Studies on its Safety and Hemostatic Potential*, J. Biomed. Mat. Res., vol. 34, pp. 21-28 (1997).

Permeation Enhancing Properties/Actions

It has also been reported that chitosan acts as a permeation enhancer by opening epithelial tight junctions. The mechanism underlying this behavior is deemed to be based on the interaction of positively charged chitosan and the cell membrane resulting in a reorganization of the tight junction-associated proteins. See Smith, et al., *Effect of Chitosan on Epithelial Cell Tight Junctions*, Pharm. Res., vol. 21(1), pp. 43-49 (2004).

Antimicrobial Properties/Actions

The antimicrobial activity of chitin, chitosan, and their derivatives against different groups of microorganisms, such as bacteria, yeast, and fungi, has also received considerable attention in recent years. Two main mechanisms have been suggested as the cause of the inhibition of microbial cells by chitosan.

The first mechanism comprises the interaction with anionic groups on the cell surface, due to chitosan's polycationic nature, causes the formation of an impermeable layer around the cell, which prevents the transport of essential solutes.

The second mechanism involves the inhibition of the RNA and protein synthesis by permeation into the cell nucleus. See Liu et al., *Antibacterial Action of Chitosan and Carboxymathylated Chitosan*, J. Appl. Polym. Sci., vol. 79(7), pp. 1324-1335 (2001).

Antioxidative Properties/Actions

Chitosan has also shown a significant scavenging capacity against different radical species; the results being comparable to those obtained with commercial antioxidants. See Park, et al., *Free Radical Scavenging Activities of Differently Deacetylated Chitosans*, Carbohyd. Polym., vol. 55(1), pp. 17-22 (2004).

Tissue Repair Properties/Actions

By virtue of the above discussed properties of chitosan, chitosan can and in most instances will, enhance the repair of damaged tissue. Indeed, it has been found that chitosan activates immunocytes and inflammatory cells, such as PMN, macrophage, fibroblasts and angioendothelial cells. See Ueno, et al., *Topical Formulations and Wound Healing Applications of Chitosan*, Adv. Drug Del. Res., vol. 52, pp. 105-115 (2001).

Chitosan oligomers have also exhibited tissue repair properties. It has been suggested that the tissue repair properties are due to their ability to stimulate fibroblast production by affecting the fibroblast growth factor. Subsequent collagen production further facilitates the formation of connective tissue.

According to the invention, the amount of chitosan added to a pharmacological composition of the invention is preferably less than 50 ml, more preferably, less than approximately 20 ml.

In some embodiments of the invention, the chitosan is incorporated in a polymeric network, such as disclosed in U.S. Pub. Nos. 2008/0254104 and 2009/0062849, which are incorporated herein in their entirety.

In some embodiments of the invention, the bioactive agent comprises a cell. According to the invention, the cell can comprise, without limitation, a stem cell, such as, for example, a human embryonic stem cell, fetal cell, fetal cardiomyocyte, myofibroblast, mesenchymal stem cell, autotransplanted expanded cardiomyocyte, adipocyte, totipotent cell, pluripotent cell, blood stem cell, myoblast, adult stem cell, bone marrow cell, mesenchymal cell, embryonic stem cell, parenchymal cell, epithelial cell, endothelial cell, mesothelial cell, fibroblast, myofibroblast, osteoblast, chondrocyte, exogenous cell, endogenous cell, stem cell, hematopoetic stem cell, pluripotent stem cell, bone marrow-derived progenitor cell, progenitor cell, myocardial cell, skeletal cell, undifferentiated cell, multi-potent progenitor cell, unipotent progenitor cell, monocyte, cardiomyocyte, cardiac myoblast, skeletal myoblast, macrophage, capillary endothelial cell, xenogenic cell, and allogenic cell.

In some embodiments of the invention, the bioactive agent comprises a protein. According to the invention, the protein can comprise, without limitation, a growth factor, collagen, proteoglycan, glycosaminoglycan (GAG) chain, glycoprotein, cytokine, cell-surface associated protein, cell adhesion molecule (CAM), angiogenic growth factor, endothelial ligand, matrikine, matrix metalloprotease, cadherin, immunoglobin, fibril collagen, non-fibrillar collagen, basement membrane collagen, multiplexin, small-leucine rich proteoglycan, decorin, biglycan, fibromodulin, keratocan, lumican, epiphycan, heparan sulfate proteoglycan, perlecan, agrin, testican, syndecan, glypican, serglycin, selectin, lectican, aggrecan, versican, nuerocan, brevican, cytoplasmic domain-44 (CD44), macrophage stimulating factor, amyloid precursor protein, heparin, chondroitin sulfate B (dermatan sulfate), chondroitin sulfate A, heparan sulfate, hyaluronic acid, fibronectin (Fn), tenascin, elastin, fibrillin, laminin, nidogen/entactin, fibulin I, fibulin II, integrin, a transmembrane molecule, platelet derived growth factor (PDGF), epidermal growth factor (EGF), transforming growth factor alpha (TGF-alpha), transforming growth factor beta (TGF-beta), fibroblast growth factor-2 (FGF-2) (also called basic fibroblast growth factor (bFGF)), thrombospondin, osteopontin, angiotensin converting enzyme (ACE), and vascular epithelial growth factor (VEGF).

According to the invention, the bioactive agents referenced above can comprise any form. In some embodiments of the invention, the bioactive component or components, e.g. simvastatin and/or chitosan, comprise microcapsules that provide delayed delivery of the agent contained therein.

Additional suitable pharmacological compositions that can be delivered within the scope of the invention are disclosed in Pat. Pub. Nos. 20070014874, 20070014873, 20070014872, 20070014871, 20070014870, 20070014869, and 20070014868; which are expressly incorporated by reference herein in its entirety.

As indicated above, in some embodiments of the invention, one or more ECM compositions of the invention are directly administered or delivered to damaged or diseased cardiovascular tissue via a unique multi-needle injection system. As will readily be appreciated by one having ordinary skill in the art, the pharmacological compositions of the invention can also be delivered to damaged tissue via one or more conventional injection apparatus and systems, e.g., syringe. According to the invention, the ECM compositions can be directly administered to the heart wall and/or the various cardiovascular structures associated therewith.

Figure 1:
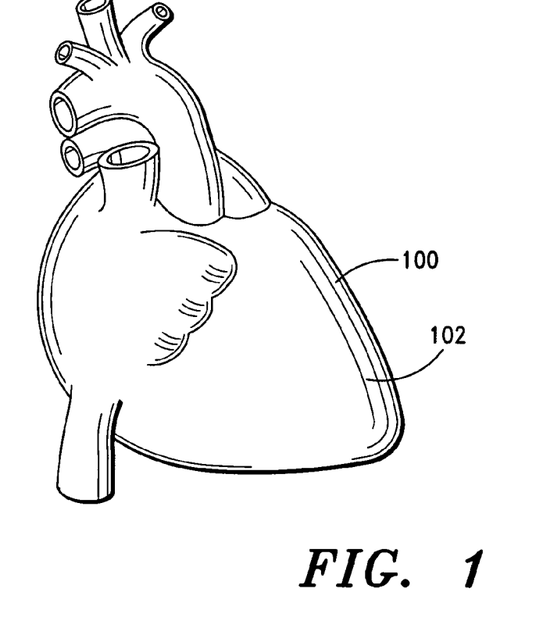
FIG. 1 is a depiction of a normal heart.

Referring now to FIG. 1 there is shown a depiction of a normal heart 100. The heart wall 102 consists of an inner layer of simple squamous epithelium, referred to as the endocardium. The endocardium overlays the myocardium (a variably thick heart muscle) and is enveloped within a multi-layer tissue structure referred to as the pericardium. The innermost layer of the pericardium, referred to as the visceral pericardium or epicardium, covers the myocardium. An outermost layer of the pericardium, referred to as the fibrous pericardium, attaches the parietal pericardium to the sternum, the great vessels and the diaphragm.

According to the invention, an ECM composition can be delivered to each of the noted structures; particularly, the myocardium, whereby neovascularization, host tissue proliferation, and bioremodeling is induced.

Figure 2:
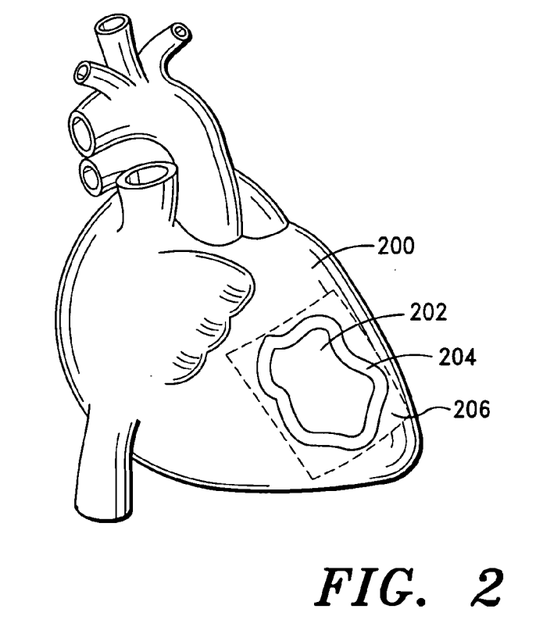
FIG. 2 is a of a heart having an ischemic infracted region.

Referring now to FIG. 2, there is shown a depiction of a heart 200 having an ischemic infracted region 202, and a peri-infarcted region 204 that is surrounded by healthy non-ischemic myocardium tissue 206.

As indicated above, a myocardial infarction, i.e. irreversible myocardial injury resulting in necrosis of a significant portion of myocardium, can result in an acute depression in ventricular function and expansion of the infarcted tissue under stress. This triggers a cascading sequence of myocellular events. In many cases, this progressive myocardial infarct expansion and remodeling leads to deterioration in ventricular function and heart failure.

When a myocardial infarction occurs, the myocardial tissue that is no longer receiving adequate blood flow dies and is replaced with scar tissue. This infarcted tissue cannot contract during systole, and may actually undergo lengthening in systole and leads to an immediate depression in ventricular function. This abnormal motion of the infarcted tissue can cause delayed or abnormal conduction of electrical activity to the still surviving peri-infarct tissue (tissue at the junction between the normal tissue and the infarcted tissue) and also places extra structural stress on the peri-infarct tissue.

In addition to immediate hemodynamic effects, the infarcted heart tissue and undergoes three major processes: infarct expansion, infarct extension, and chamber remodeling.

These factors individually and in combination contribute to the eventual dysfunction observed in the cardiac tissue remote from the site of the infarction.

Infarct expansion is a fixed, permanent, disproportionate regional thinning and dilatation of tissue within the infarct zone. Infarct extension is additional myocardial necrosis following myocardial infarction. Infarct extension results in an increase in total mass of infarcted tissue.

However, as indicated above, the noted effects of a myocardial infarction can be ameliorated or eliminated by administering an ECM composition of the invention directly to the infarcted cardiovascular tissue. As also indicated herein, the ECM compositions of the invention will specifically induce neovascularization, host tissue proliferation, bioremodeling, and regeneration of new cardiac tissue structures with site-specific structural and functional properties. A preferred means of administering the ECM compositions to infracted cardiovascular tissue comprises direct injection via the multi-needle injection apparatus 300 illustrated in FIGS. 3A and 3B and the associated control system described in Co-Pending Application No. 61/704,634.

EXAMPLES

The following examples are provided to enable those skilled in the art to more clearly understand and practice the present invention. They should not be considered as limiting the scope of the invention, but merely as being illustrated as representative thereof.

Example 1

Five (5) porcine hearts were obtained from young calves. After removal, the hearts were stored in a saline bath.

A first heart was removed from the bath. The thickness of the heart wall was determined to range from 4 mm to greater than 2 cm with an A scan ultrasound sensor.

A multi-needle injection system of the invention, such as illustrated in FIGS. 2 and 3 was provided and prepared for the injection procedure.

An ECM composition of the invention was also provided. The ECM composition comprised two components: an ECM (i.e. SIS) particulate derived from porcine intestines and a SIS gel. The SIS particulate comprised SIS material, which was cryogenically ground to a characterized particle size, and subsequently thawed and loaded into a syringe for delivery. The particulate size was in the range of 50-350 microns.

The SIS gel comprised SIS material that was cryogenically ground, subject to enzymatic digestion in acid, lyophilized, and reconstituted to a predetermined concentration. The SIS gel was also subjected to a subsequent disinfection and neutralization process. The SIS gel was also loaded into a syringe.

The materials were maintained in refrigerated conditions throughout processing.

Approximately 4 cc of SIS gel was mixed with 6 cc of particulate SIS to derive an injectable ECM composition.

The injectable ECM composition was then transferred into the reservoirs of the injector apparatus.

The injector control system was then set to provide the following delivery parameters: two (2) equal pulses at 20 and 30 milliseconds and at pressures ranging from approximately 60-120 psi. The noted parameters provided an ECM composition delivery in the range of approximately 0.5-1.0 ml per pulse.

The ECM composition was then delivered into the wall of a first heart. The injected portion of the heart wall was then observed visually and with a B scan ultrasound (i.e. echo) sensor to assess the ECM composition delivery pattern. Substantially uniform delivery (i.e. amount and spread) at each needle injection site was observed.

The injected portion of the heart wall was also sectioned to observe the delivery pattern. The procedure confirmed that delivery was uniform and at the prescribed needle depth at each needle injection site, with a good safety margin from the ventricular cavity.

The above noted test procedures were similarly employed with the remaining four (4) porcine hearts. The only parameter that varied was the proportion of SIS gel in the ECM composition.

In the second heart, the ECM composition was similar to the ECM composition employed for the first heart, i.e. approximately 4 cc of SIS gel and 6 cc of particulate SIS.

In the third and fourth hearts, the ECM composition comprised approximately 2 cc of SIS gel and 8 cc of particulate SIS.

In the fifth heart, no SIS gel was employed. The ECM composition thus comprised approximately 10 cc of particulate SIS.

In each instance, the delivery was similarly uniform and at the prescribed needle depth at each needle injection site, with a good safety margin from the ventricular cavity.

Example 2

A young porcine was provided in which CHF had been induced via serial microsphere injections down the coronary arteries.

A multi-needle injection system of the invention, such as illustrated in FIGS. 2 and 3, was prepared for injection of an ECM composition of the invention.

An ECM composition, such as described in Example 1, was also provided. The composition mixture comprised approximately 4 cc of SIS gel was mixed with 6 cc of particulate SIS to derive an injectable ECM composition.

The injectable ECM composition was then transferred into the reservoirs of the injector apparatus.

The injector control system was similarly set to provide the following delivery parameters: two (2) equal pulses at 20 and 30 milliseconds and at pressures ranging from approximately 60-120 psi. The noted parameters provided an ECM composition delivery in the range of approximately 0.5-1.0 ml per pulse.

The heart of the porcine was then exposed. A B scan ultrasound sensor was then employed to assess the depth of the infarcted region.

The ECM composition was then delivered into the infarcted region. The injected portion of the heart wall was then observed visually and with a B scan ultrasound (i.e. echo) sensor to assess the ECM composition delivery pattern. Substantially uniform delivery (i.e. amount and spread) at each needle injection site was observed. The ECM composition also stayed within the infarcted region without coming out of the ventricle wall.

Further, no extravasation or emboli was observed.

A ventricular assist device was subsequently placed into the apex and the animal recovered without incident.

In accord with the invention, within 2-4 weeks, neovascularization, host tissue proliferation, bioremodeling and regeneration of new tissue proximate the infracted region will be observed.

As will readily be appreciated by one having ordinary skill in the art, the present invention provides numerous advantages compared to prior art methods and systems for treating damaged cardiac tissue. Among the advantages are the following:

- The provision of pharmacological compositions which, when delivered to damaged biological tissue; particularly, cardiovascular tissue, induce neovascularization, and promote survival and regeneration of damaged cardiovascular tissue.
- The provision of extracellular matrix (ECM) compositions which, when delivered to damaged biological tissue; particularly, cardiovascular tissue, induce host tissue proliferation, bioremodeling, and regeneration of cardiovascular tissue structures with site-specific structural and functional properties.
- The provision of improved methods and systems for administering pharmacological compositions; particularly, ECM compositions directly to damaged or diseased biological tissue.

Without departing from the spirit and scope of this invention, one of ordinary skill can make various changes and modifications to the invention to adapt it to various usages and conditions. As such, these changes and modifications are properly, equitably, and intended to be, within the full range of equivalence of the following claims.

What is claimed is:

1. A composition for reducing inflammation of damaged cardiovascular tissue and inducing regeneration of cardiovascular tissue, comprising:
   an extracellular matrix (ECM) composition comprising acellular small intestine submucosa (SIS),
   and 0.1 µM of an added cerivastatin, said ECM composition further comprising transforming growth factor-β (TGF-β), wherein said cerivastatin is mixed with said ECM composition, wherein a statin-growth factor augmented ECM composition is formed, and wherein, when said statin-growth factor augmented ECM composition is administered to damaged cardiovascular tissue, said statin-growth factor augmented ECM composition inhibits localized expression of proinflammatory chemokine monocyte chemoattractant protein-1 (MCP-1) and proinflammatory receptor C—C chemokine receptor type-2 (CCR2),
   whereby, said statin-growth factor augmented ECM composition reduces inflammation of said damaged cardiovascular tissue and induces bioremodeling and regeneration of new cardiovascular tissue.

2. The composition of claim 1, wherein said ECM composition further comprises an additional growth factor selected from the group consisting of fibroblast growth factor-2 (FGF-2) and vascular endothelial growth factor (VEGF).

* * * * *